(12) United States Patent
Vlachomitrou et al.

(10) Patent No.: US 11,723,610 B2
(45) Date of Patent: Aug. 15, 2023

(54) METHOD AND DEVICE FOR CREATING A CEPHALOMETRIC IMAGE

(71) Applicant: TROPHY, Croissy Beaubourg (FR)

(72) Inventors: Anna-Sesilia Vlachomitrou, Croissy Beaubourg (FR); Vincent Loustauneau, Fontenay sous Bois (FR)

( * ) Notice: Subject to any disclaimer, the term of this patent is extended or adjusted under 35 U.S.C. 154(b) by 198 days.

(21) Appl. No.: 17/203,222

(22) Filed: Mar. 16, 2021

(65) Prior Publication Data

US 2022/0031264 A1 Feb. 3, 2022

Related U.S. Application Data

(63) Continuation of application No. 16/065,803, filed as application No. PCT/IB2015/002510 on Dec. 23, 2015, now abandoned.

(51) Int. Cl.

| A61B 6/14 | (2006.01) |
|---|---|
| A61B 6/02 | (2006.01) |
| A61B 6/03 | (2006.01) |
| A61B 6/06 | (2006.01) |
| A61B 6/00 | (2006.01) |
| G06T 11/00 | (2006.01) |

(52) U.S. Cl.
CPC ............... *A61B 6/14* (2013.01); *A61B 6/025* (2013.01); *A61B 6/027* (2013.01); *A61B 6/032* (2013.01); *A61B 6/06* (2013.01); *A61B 6/4085* (2013.01); *A61B 6/4233* (2013.01); *A61B 6/4435* (2013.01); *A61B 6/5205* (2013.01); *A61B 6/5235* (2013.01); *A61B 6/5258* (2013.01); *G06T 11/006* (2013.01); *A61B 6/4266* (2013.01); *G06T 2211/421* (2013.01); *G06T 2211/424* (2013.01)

(58) Field of Classification Search
CPC ........... A61B 6/14; A61B 6/025; A61B 6/027; A61B 6/032; A61B 6/06; A61B 6/4085; A61B 6/4233; A61B 6/4435; A61B 6/5205; A61B 6/5235; A61B 6/5258; A61B 6/4266; G06T 11/006; G06T 2211/421; G06T 2211/424
See application file for complete search history.

(56) References Cited

U.S. PATENT DOCUMENTS

| 2009/0041191 A1* | 2/2009 | Suzuki | A61B 6/488 378/98.5 |
|---|---|---|---|
| 2010/0034340 A1* | 2/2010 | Spartiotis | A61B 6/588 378/4 |

\* cited by examiner

*Primary Examiner* — Christine S. Kim

(57) ABSTRACT

An extra-oral dental imaging system comprises an X-ray source (102) and an imaging device (101) suitable for producing multiple frames during at least part of an exposure of an object (200), the imaging device (101) being displaced along a scanning direction (X). A method for creating a cephalometric image of a human skull comprises a step of setting said imaging device (101) with an active area having in an imaging plane a width extending along said scanning direction (X), said width varying along a height direction perpendicular to said scanning direction (X); a step of synchronously displacing the X-ray source (102) and the imaging device (101) along said exposure profile; and a step of registering multiple frames produced by the imaging device (101) during the exposure of said object (200) to be imaged. Using for creating a cephalometric image by digital tomosynthesis.

21 Claims, 10 Drawing Sheets

METHOD AND DEVICE FOR CREATING A CEPHALOMETRIC IMAGE

FIELD OF THE INVENTION

The present invention concerns a method for creating a cephalometric image as well as a related system.

The present invention relates to the field of dental extra-oral imaging systems.

More specifically, the present invention relates to cephalometric imaging, namely a linear projection of the human skull or part of the human skull.

BACKGROUND

The 2D cephalometric radiograph is an imaging technique which produces a linear projection of a human head on a flat 2D sensor (or, in more general terms, an imaging layer of an imaging device).

Cephalometric analysis is a technique commonly employed by orthodontists, dentists, et al. to analyze the dimensional relationships in the craniofacial complex, to predict future changes, to assess the effect of ongoing treatment plans, to evaluate the patient's dentomaxillofacial proportions, and to aid in the diagnosis of abnormalities and asymmetries.

Consequently, there is a need for a system which produces high-resolution cephalometric images.

A planar imaging system has two types of resolution: an in-plane spatial resolution, in the direction parallel to the imaging layer of the imaging device; and a depth resolution, perpendicular to the imaging layer of the imaging device.

The image depth resolution depends primarily on the width of the sensor along the direction of movement and the actual movement trajectory.

In the known extra-oral systems for performing panoramic imaging, the sensor is typically narrow in aspect, long and with a small width. In order to obtain a linear projection of the entire human skull (cephalometric image), the imaging system includes a cephalometric or "ceph" arm: the panoramic sensor is attached on the "ceph" arm in the cases where a cephalometric image is needed.

As a consequence, a large distance is provided between the X-ray source and the sensor, in order to minimize distortions and magnification disproportions in the projected image. Such a cephalometric arm is cumbersome. Moreover, this technique creates a cephalometric image where both the left and right sides of the patient's cranium are superimposed at different degrees of magnification, which can result in image distortion and may be of limited diagnostic and therapeutic utility.

The document U.S. Pat. No. 8,306,181 discloses an extra-oral dental imaging system with a sensor capable of producing a cephalometric image without the use of an additional "ceph" arm.

An elongated rectangular sensor is used with an aspect ratio m:n superior to 1.5, wherein m is the long dimension of the active area of the sensor and n is the short dimension of the active area of the sensor.

The sensor and the X-ray source are displaced together along a trajectory divided into three segments: a first exposure, a non-radiating movement and a second exposure. During the two exposure segments, the left and right side of the skull are imaged.

The two segments of the profile during which the skull is exposed to radiation are substantially linear. The length of the linear exposure is generally more than 5 cm, but in any case long enough to produce data that can be used to produce a volumetric reconstruction of an image to be displayed.

The distance between the focal point of the X-ray source and the imaging device is small compared to the standard case with the "ceph" arm.

After the exposures, a volumetric reconstruction algorithm is used to calculate vertical slices along the imaging direction. The content of each individual slice is reconstructed using tomosynthesis techniques. The vertical slices are then transformed to eliminate different magnification factors of different vertical slices, and then added together to produce a 2D cephalometric image or 2D cephalogram.

A volume reconstruction with an acceptable depth resolution necessitates the use of a sensor with an active area that is sufficient in the scanning direction. By "active area," it is meant the area of the sensor which is irradiated during the scan and which actually participates in the image reconstruction process.

It has been observed that the use of an active area in the shape of a narrow strip is inappropriate for realizing a three-dimensional reconstruction of acceptable quality. On the other hand, the larger the size of the x-ray sensor in the scanning direction, the larger the x-ray dose must be administered to the patient. In other words, having a high depth resolution is disadvantageous in that it requires a high x-ray dosage to the patient.

It is noted that what constitutes a sufficient depth resolution depends on the part of the body being imaged. However, certain parts of the body, either because they are not of primary importance from a diagnostic or therapeutic standpoint or because they are simply not complex structures, do not need to be reconstructed with a high level of detail. For example, while the mandibles and dentition must be imaged with a great deal of detail, the rest of the skull can be imaged at a much lower level of detail and still produce a useful image. Such parts generally comprise a lower number of anatomical "landmarks," and thus a lower depth resolution is satisfactory.

There is thus a need for a system and method for imaging that is able to adapt the depth resolution, and by extension the local radiation dose, to the structure of the irradiated anatomy.

The present invention aims to address, in whole or in part, at least the foregoing and other deficiencies in the related art.

SUMMARY OF THE INVENTION

According to one aspect of the disclosure, there is provided a method for creating a cephalometric image of at least part of a human skull in an extra-oral dental imaging system, said system comprising an X-ray source for irradiating an object to be imaged; an imaging device suitable for producing multiple frames during at least part of an exposure of said object; a manipulator for displacing the imaging device along an exposure profile between multiple frames during said at least part of the exposure of said object, the manipulator permitting the movement of the imaging device along a scanning direction.

According to the invention, said method comprises steps of setting said imaging device with an active area having in an imaging plane a width, extending along said scanning direction, said width varying along a height direction perpendicular to said scanning direction; synchronously displacing the X-ray source and the imaging device along said exposure profile; and registering said multiple frames produced by the imaging device during the exposure of said object to be imaged.

Due to the use of an imaging device with an active area varying in the height of the imaging device, the depth resolution may be adapted to the regions of interest of a human skull for creating a cephalometric image.

Such an adapted active area of the imaging device provides a good compromise between the depth resolution obtained in a direction perpendicular to the plane of the image (needed for creating the cephalometric image), and the X-ray dose on the patient skull.

Thus, thanks to the 3D information, an accurate landmarking may be generated and precise reference points may be used for the cephalometric analysis. Preferably, said active area is symmetric in said imaging plane, with a central axis extending along said height direction of said active area.

This is advantageous in that the method can be executed to scan from both the left and right sides of the head, without any deformation or visual artifacts provoked by the asymmetry of the active area.

In a possible embodiment, said active area has at least two portions having widths different from each other, said two portions being superposed in said imaging plane along said height direction.

In possible embodiments, the height of the active area is between 120 mm and 280 mm, with the width of the first portion being between 2 mm and 50 mm and the width of the second portion being between 50 mm and 140 mm.

In an advantageous embodiment, said active area has at least three portions with respectively three different widths.

This is advantageous in that, through the use of at least three active portions, the depth resolution of the scan is more closely tailored to the anatomy being scanned.

Most preferably, said active area has a central portion, a lower portion, and an upper portion each extending along said height direction in said imaging plane, the width of the central portion is larger than the width of the lower portion and the width of the lower portion is larger than the width of the upper portion.

The three portions can be made to correspond to three regions of the anatomy for which cephalographs are of particular interest: the cranium, the jaw and dentition, and the chin and vertebrae.

Since each of these regions has a different level of structural complexity, the widths of each of the portions can be made to correspond to the desired level of depth resolution for the region to which it corresponds.

Such a configuration of the active area gives a good differentiation in depth resolution, along with acceptable levels of X-ray dosing, for many medical applications.

In a possible embodiment, the method further comprises a step of computing the multiple frames produced during at least one part of the exposure by a shift-and-add processing, thereby reconstructing at least one slice; or by a volumetric approach, thereby reconstructing a three-dimensional volume and subsequently extracting at least one slice from said volume; said at least one slice from said volume containing in-focus imaging data belonging respectively to at least one depth of said object to be imaged.

In this way, a three-dimensional model of the patient's anatomy is constructed, providing high-resolution, high-precision information that is not limited to a narrow "focal trough" but is rather of a consistently high quality through the entire depth of the scan.

Moreover, from this model, high-quality simulations of conventional imaging scans can easily be extracted and/or extrapolated, maximizing the diagnostic and therapeutic utility of each scan.

In possible embodiments, the volumetric approach is selected from a Statistical Algebraic Reconstruction Technique (SART), a Statistical Iterative Reconstruction Technique (SIRT), or a Filtered Back Projection Technique.

Such approaches are advantageous in that they yield a high-quality reconstruction of the subject while limiting the X-ray dosage incurred. In particular, certain a priori information is employed so as to refine the reconstruction, such as the positions of certain anatomical features in the patient's cranium. This in turn refines the reconstruction and improves the quality of the images produced from it.

Preferably, the method further comprises a step of using each reconstructed slice for the extraction of cephalometric features.

Most preferably, in a step of automatic cephalometric tracing, said extracted cephalometric features of each slice are put together.

In this way, a complete cephalometric image is constructed, thereby enabling e.g. a dentist to perform diagnostic and therapeutic procedures based thereupon.

In a possible variant embodiment, several slices are reconstructed and combined to give a separate linear projection for the left and right sides of said object to be imaged.

In this way, a pair of cephalometric images is constructed with a single scan, reducing X-ray dosage to the patient while providing bilateral cephalometric information.

In another possible variant embodiment, several slices are reconstructed and retro-projected to a distance superior to 1.50 meters, and preferably superior to 4 meters, on a cone beam or parallel geometry so as to create a synthesized 2D cephalogram of the skull.

This is advantageous in that a traditional 2D cephalogram is produced, without requiring an extra "ceph arm" or the space to accommodate it, or any additional X-ray exposure to the patient.

According to another embodiment, the method for creating a cephalometric image of a part of a human skull comprises the following steps:

synchronously displacing the X-ray source and the imaging device along a first part of said exposure profile, said X-ray source being in an upper position along said height direction;

registering said multiple frames produced by the imaging device during said first part of the exposure profile;

synchronously displacing the X-ray source and the imaging device along a second part of said exposure profile, said X-ray source being in a lower position along said height direction;

registering said multiple frames produced by the imaging device during said second part of the exposure profile; and combining said multiple frames registered during said first and second parts of the exposure profile.

Thus, the patient skull is scanned with an X-ray source at several discrete positions along the height direction.

According to another aspect, there is provided an extra-oral dental imaging system for creating a cephalometric image of at least part of a human skull, such system comprising an X-ray source for irradiating an object to be imaged, an imaging device suitable for producing multiple frames during at least part of an exposure of said object; a manipulator for displacing the imaging device along an exposure profile between multiple frames during said at least part of the exposure of said object, the manipulator permitting the movement of the imaging device along a scanning direction According to the invention, said imaging device has an active area having in an imaging plane a width extending along said scanning direction, said width varying along a height direction perpendicular to said scanning direction; and said manipulator synchronously displaces the X-ray source and the imaging device along said exposure profile; and said imaging device comprises memory for registering said multiple frames produced by the imaging device during the exposure of said object to be imaged.

Such an apparatus is advantageous in that it realizes the advantageous aspects of the method and variants described above.

BRIEF DESCRIPTION OF THE DRAWINGS

The foregoing and other objects, features and advantages of the invention will be apparent from the following more particular description of the embodiments of the invention, as illustrated in the accompanying drawings.

The elements of the drawings are not necessarily to scale relative to each other. Some exaggeration may be necessary in order to emphasize basic structural relationship or principles of the invention. Some conventional components that would be needed for implementation of the described embodiments, such as support components used for providing power, for packaging, and for mounting and protecting x-ray system components, for example, are not shown in the drawings in order to simplify the description.

FIG. 1A illustrates the general configuration of an extra-oral dental imaging system 100 according to a first embodiment of the invention. The imaging system 100 comprises a sensor 101 and an X-ray source 102. The sensor 101 and the X-ray source 102 are mounted in this embodiment on a gantry 103 which is itself fastened to a horizontal mount 104.

Figure 1A:
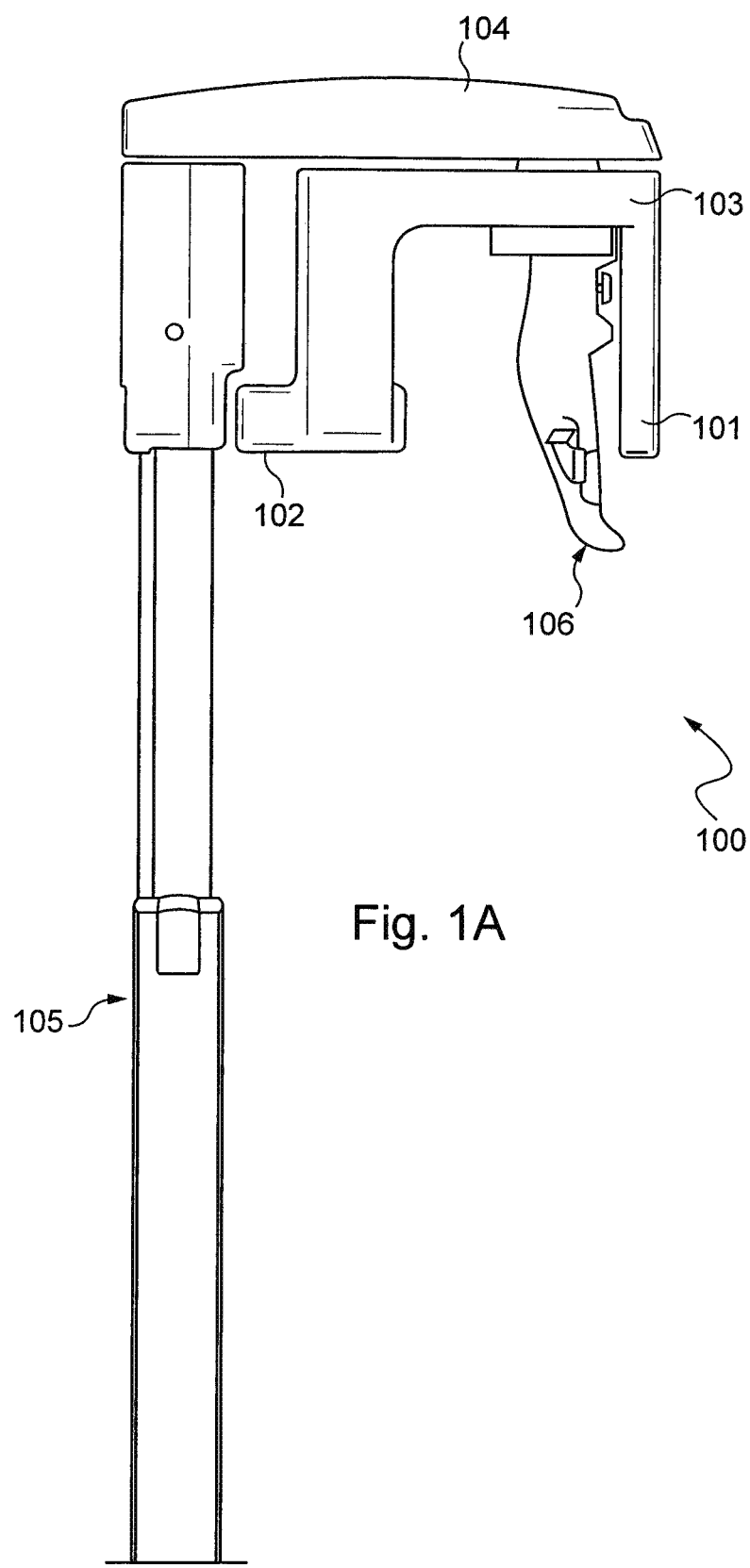
FIG. 1A is a diagram showing a perspective view of an extra-oral dental imaging system according to a first embodiment of the invention.

The horizontal mount 104 is fixed to a vertical column 105 which may comprise classical telescopic means not disclosed here below, permitting to set the height of the imaging system.

The imaging system also comprises a patient holder 106 which maintains the patient head in a defined and fixed position under the gantry 103, between the X-ray source 102 and the sensor 101 during the imaging process.

The patient holder 106 may be similar to a patient holder used, in prior art, on a cephalometric imaging arm to maintain the patient head during the exposure.

Figure 1B:
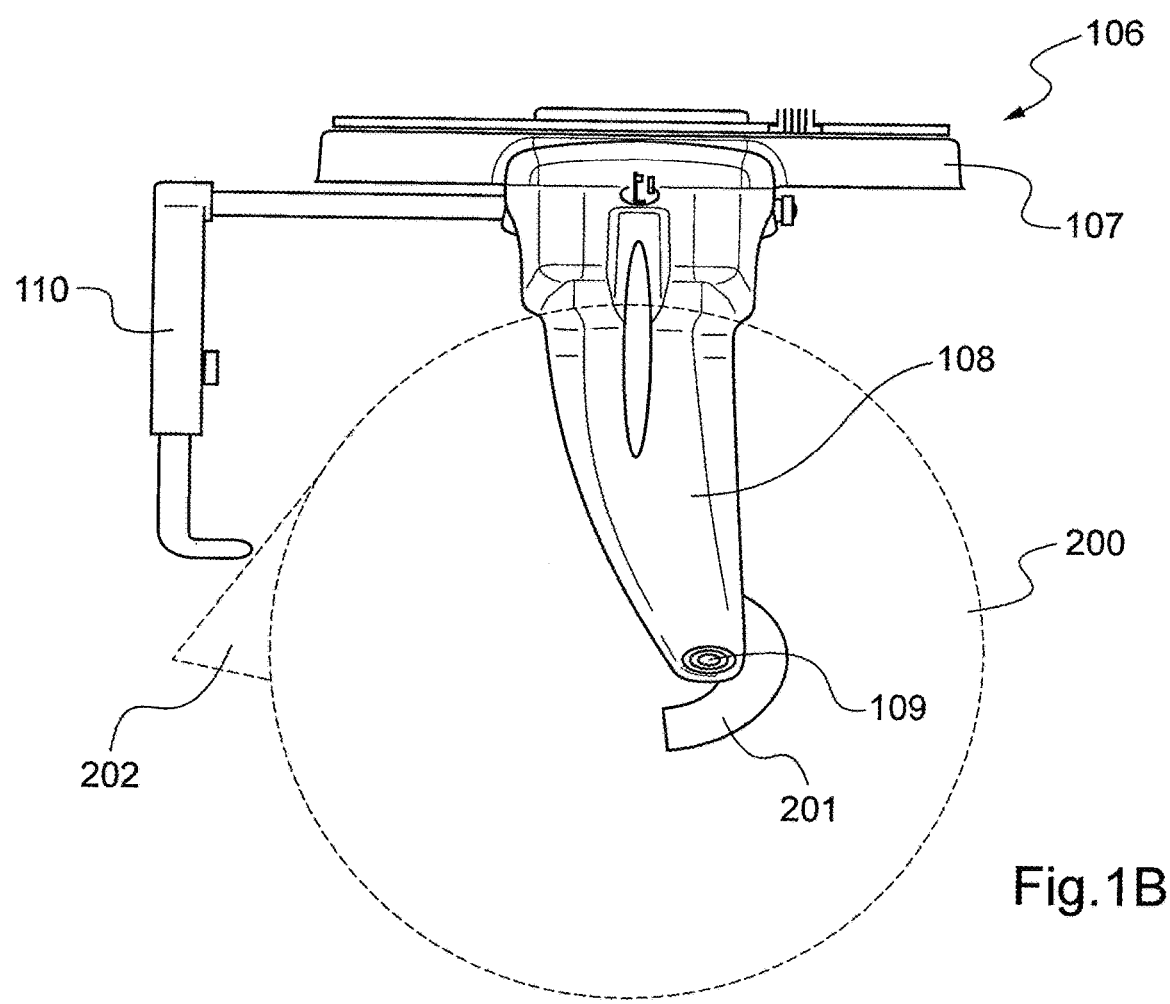
FIG. 1B is a detail of an alternate configuration of a patient support for the imaging system of FIG. 1A.

As an alternative embodiment, the patient holder 106 may be composed of two ear rod holders 108 supporting two ear rods 109 to be inserted in the patient's ear canals 201, as illustrated in FIG. 1B. The two ear rod holders are symmetrically slideable on each side to adjust to the width of the patient's head 200.

A nosepiece 110 is adjustable in the horizontal and vertical directions to be positioned exactly at the bridge (nasion) of the patient's nose 202. The ear rods 109 inserted into the ear canals 201 of the patient block any possible movement of the patient's head, except the rotation of the head about an axis passing through the two ear rods 109.

The nosepiece 110 thus serves to prevent such movement, constraining the patient's movement in this last degree of freedom. A mount 107 supports the ear rod supports 108 and the nosepiece 110, and can be fitted on the mount 104 of the imaging device through the gantry 103.

In an alternative embodiment, the patient holder 106 can be fixed with an arm (not represented on the vertical column 105); this will allow, in certain situation, a greater deal of freedom in the configuration and operation of the imaging system.

The X-ray source 102 is adapted to irradiate the object to be imaged, and in this embodiment, at least a part of a human skull for creating a cephalometric image.

The sensor 101 forms an imaging device suitable for producing multiple frames during the exposure of the object to be imaged.

In one embodiment, it is envisioned that the X-ray sensor 101 is a charge-coupled device (CCD), a CMOS sensor, or a TFT sensor, as such a device could be easily integrated into a computerized imaging system with minimal adaptation.

The gantry 103 forms a manipulator for displacing the sensor 101 and the X-ray source 102 along an exposure profile.

Thus, the manipulator or gantry 103 permits the movement of the X-ray source 102 and the sensor 101 by means of a selective translation and a selective rotation.

Figure 1C:
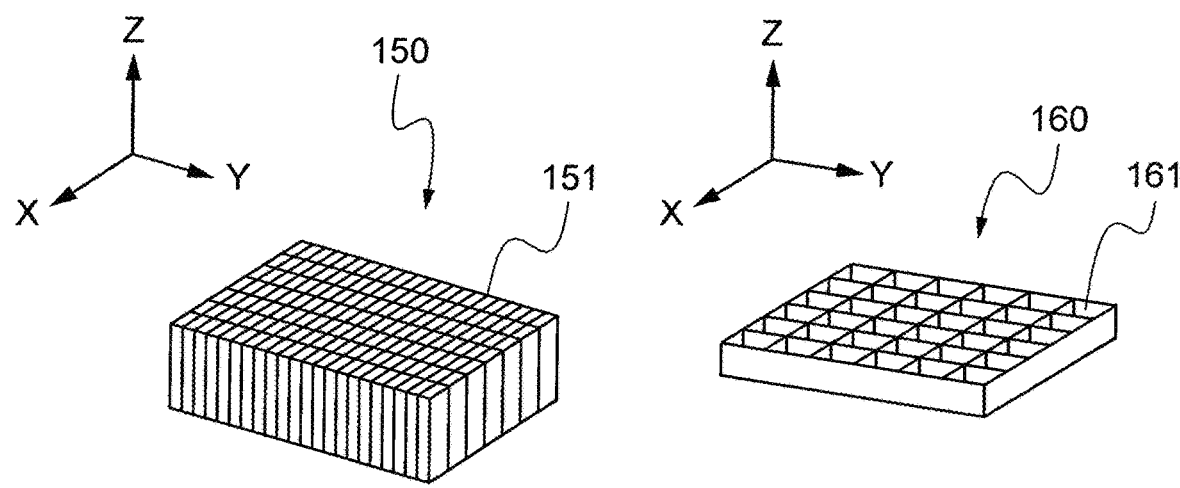
FIG. 1C is a representation of the voxel size and shape realized by the method of the invention and a scan according to a CBCT method of the art.

FIG. 1C illustrates the result of the invention as compared to that of a Cone-Beam Computerized Tomography (CBCT) technique as known in the art. The grid 150 is a representation of the result of the method of the present invention, while the grid 160 is representative of the result of the CBCT method. In particular, it can be seen that the area in the x-y plane of each of the "blocks" 151 is very small compared to the blocks 161, meaning that the in-plane resolution of the method according to the present invention is very high compared to that of the CBCT method.

On the other hand, the depth resolution is not as fine (as can be seen in the increased height of the grid 150 relative to the grid 160). However, for cephalometric purposes the depth resolution of the method of the present invention is nonetheless acceptable, and the x-ray dosage remains very low compared to CBCT.

Figure 2:
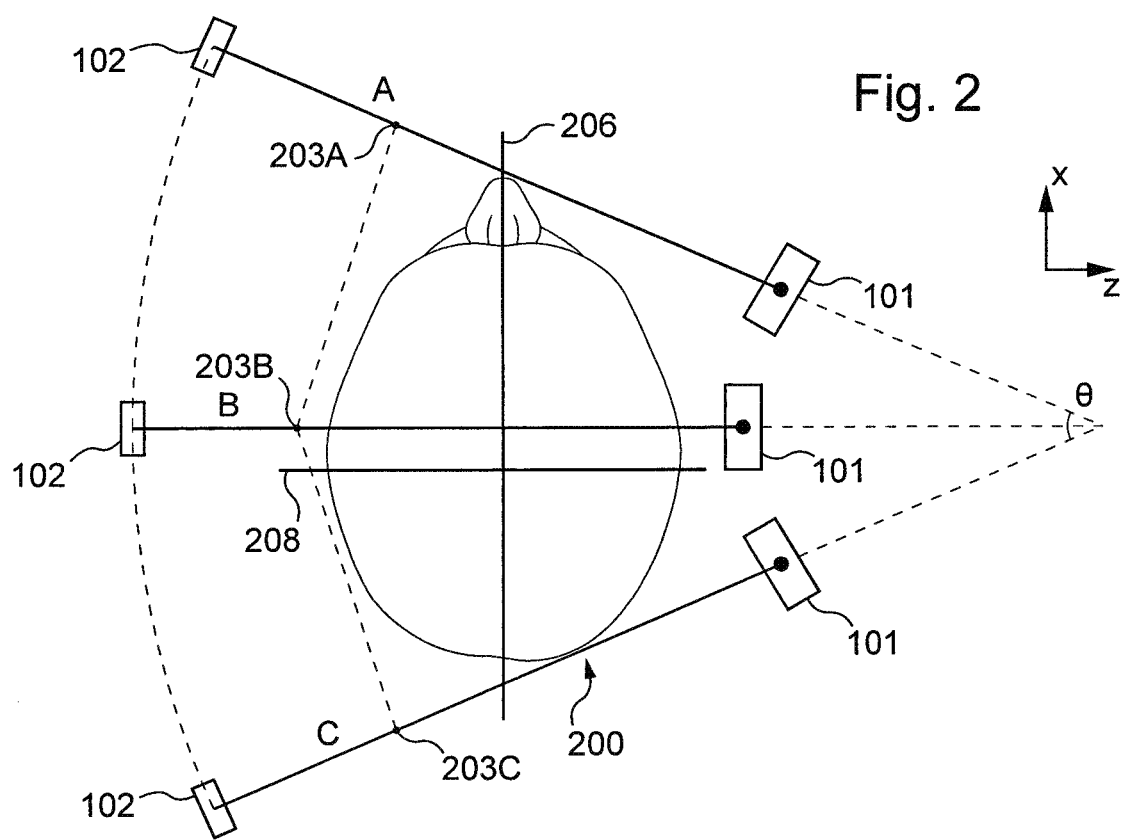
FIG. 2 is a diagram showing an exemplary exposure profile performed in a method for creating a cephalometric image according to a first embodiment of the invention.

Turning now to FIG. 2, the exposure profile of the imaging system 100 is illustrated in greater detail.

The exposure profile is performed for instance when creating a cephalometric image of a part of human skull.

During the exposure of the patient 200, the X-ray sensor 101 is suitable for producing multiple frames.

As known in an extra-oral dental imaging system, it comprises a memory for registering the frames produced by the imaging device.

In this embodiment, the imaging system comprises a memory for registering the multiple frames produced by the X-ray sensor 101 during the exposure of the patient skull.

The imaging system 100 is first positioned about a patient 200, such that the sensor 101 and the X-ray source 102 are disposed in an initial position A. The initial position A of the X-ray sensor 101 and the X-ray source 102 are such that a line drawn between them lies just forward of the face of the patient 200.

The X-ray sensor 101 and the X-ray source 102 are swept past the patient 200 as displayed in FIG. 2; more specifically, the X-ray sensor 101 and the X-ray source 102 are shown in the initial position A mentioned above, a final position C, and an intermediate position B between the initial position A and the final position C.

The effect of this displacement is twofold: the X-ray sensor 101 and the X-ray source 102 are rotated through an angle θ, while simultaneously translating along an X-axis from the initial position A to the end position C.

Thus, the X-ray source 102 and the X-ray sensor 101 are synchronously displaced along the exposure profile as depicted in FIG. 2. The exposure profile comprises at least one substantially linear section between the initial position A and the end position C.

As illustrated in FIG. 2, the X-ray source 102 and the X-ray sensor 101 are translated while rotating in the same direction. The angular range θ of the rotational movement of the sensor 101 and the X-ray source 102 is at least equal to 15°, and preferably equal to 30°.

In this way, thanks to the limited rotation of the sensor 101 and the X-ray source 102, the profile of the patient is irradiated and imaged with an almost perpendicular angular incidence; the curvature of the trajectory of the x-ray source 102 and the x-ray sensor 101 are exaggerated here for illustrative purposes. The trajectory of the gantry can be considered in gross as being a substantially linear path, in that the rotation of the gantry is minimal relative to its translation.

As can be seen in FIG. 2, the patient is positioned close to the sensor 101, so that the distance between the sensor 101 and the patient 200 is lower than the distance between the patient 200 and the x-ray source 102. This limits the distortion of the image due to the conical shape of the x-ray beam emitted by the x-ray source 102.

The curvature of the trajectory of the x-ray source 102 is directed towards the patient 200, and the curvature of the trajectory of the sensor 101 is directed away from the patient. There thus exists an instantaneous center of rotation that is located on the other, side of the sensor 101 from the x-ray source 102. As the patient 200 is located close to the sensor 101, the distance between the patient and the instantaneous center of rotation is minimized when the instantaneous center of rotation is on the side of the sensor 101, as illustrated in FIG. 2, resulting in a higher depth resolution.

For any volume element (voxel) position, it is ideal that the average directions of all rays passing through said position to match as closely as possible the ray direction of a true 2D cephalometric image, i.e. that which would be produced by an apparatus with the sensor placed at the end of the long "ceph arm" mentioned above. This in turn means that the tomosynthesis blur function will have minimal magnification and distortion artifacts.

This top view of the system does not show the path of the x-rays in the Z-direction. The average ray direction of CBCT x-rays will have a Z-component whose magnitude increases with distance from the primary plane. This means that the blur (associated with the limited tomosynthetic depth resolution) will "smear" anatomic features in a direction other than the ray direction of true two-dimensional cephalometric rays. The direction of this smear will align less closely with the true (and desired) 2D cephalometric ray direction as the rays pass through anatomy that is further form the plane and closer to the head and neck of the patient. Without highly accurate (i.e. fine) depth resolution, this will lead to blurring in a simulated cephalometric reprojection of the data outside of a very thin focal trough.

In the CBCT process, this depth resolution is created from the information captured by multiple x-ray beam paths through each voxel from the CBCT projections. If the sensor 101 were very large such that the entire head, or nearly the entire head, were captured in each projection, there would be a lot of flexibility allowed in the sequence of projections and the capture geometry used. The medium-sized sensor 101 of the apparatus 100 limits the geometry of the capture as subsections of the anatomy must be captured with each projection and then combined by image-processing methods to "stitch" together the image of the entire head.

In the present invention, however, rotation through the scan tilts the sensor 101 so that it is not contained within a single plane. A center of rotation 203 (numbered here as 203A, 203B, and 203C to correspond to the three positions A, B, and C of the gantry 103) is moved with an X component (along the sagittal plane of the patient 200). The center of rotation 203, in addition to moving in the X-direction (i.e. the sagittal direction), also moves a much smaller amount in the Z-direction (i.e. the coronal direction) in the case of a cephalometric scan as depicted in FIG. 2. Moreover, the center of rotation 203 is positioned above the patient's head 200 and on the same side of the X-ray source 102 (in FIG. 2, the left-hand side).

The general "convex" scan path illustrated in FIG. 2 balances all of these requirements. The exact scan path will depend, of course, on the system components and imaging requirements, such as any constraints on the movement of the center of rotation, the size of the sensor 101, and the size requirements and constraints placed upon the system by patient anatomy.

More precisely, the sensor 101 and the X-ray source 102 are aligned in front of each other according to a direction substantially parallel to the coronal direction 208, and thus perpendicular to the mid-sagittal plane 206.

Moreover, the length of the substantially linear section is comprised between 70 and 250 mm. In a general way, the length is sufficient to sweep the whole profile of the patient skull. The speed of the translation of the gantry 103 is typically about 4 centimeters per second.

Of course, it will be recognized that the exposure profile may be performed in a direction opposite from that illustrated in FIG. 2 without any substantial effect on the accuracy or resolution of the imaging process.

Thus the almost linear exposure profile through the midsagittal direction can provide a lateral cephalogram of the skull of the patient 200.

Of course, the exposure profile depicted in FIG. 2 is only a way of example: a substantially linear exposure profile through the coronal direction can provide a frontal cephalogram and a substantially linear exposure profile through a plane angled compared to the sagittal direction can provide a tilted cephalogram.

Figure 3A:
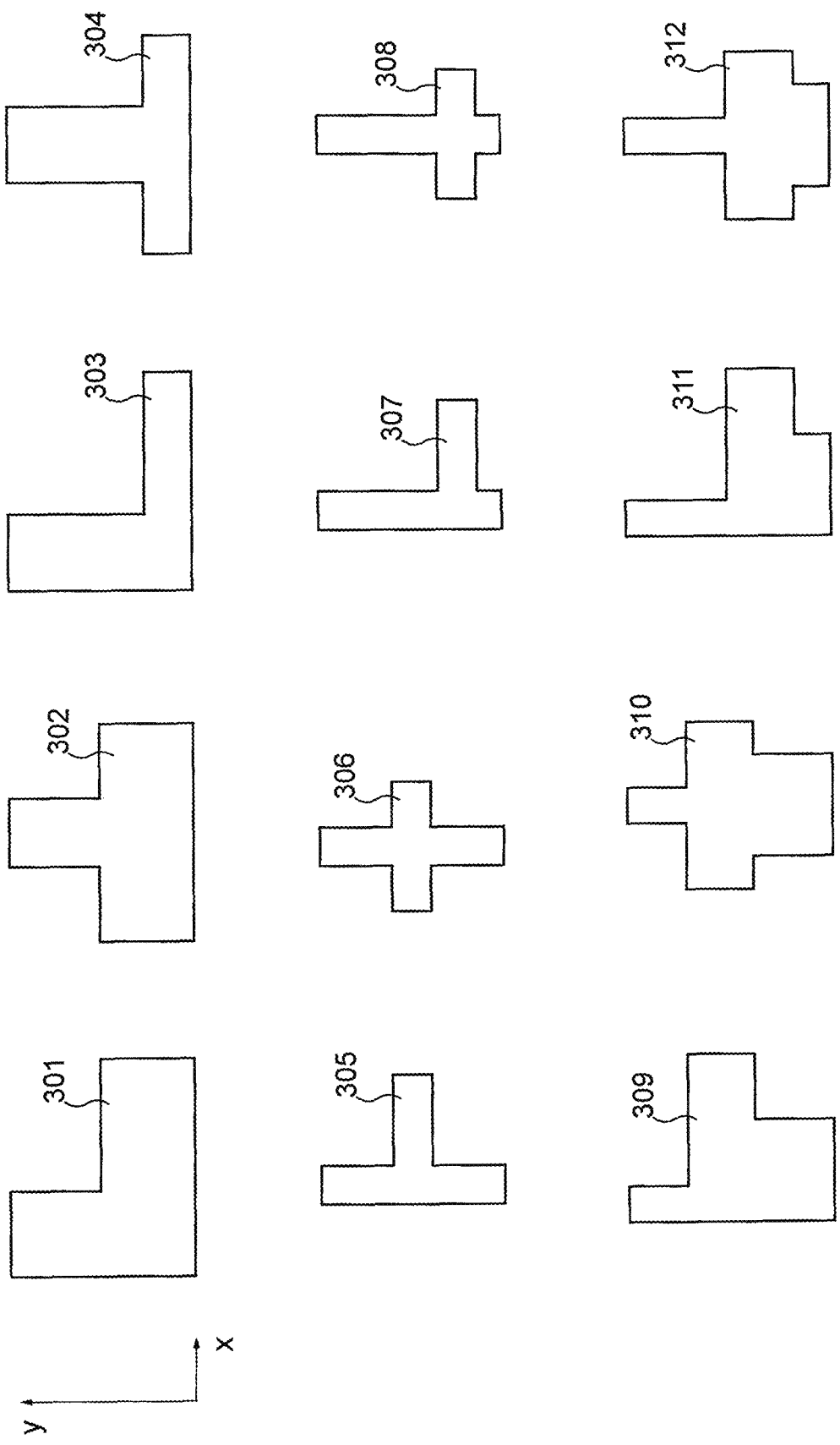
FIGS. 3A and 3B are diagrams showing exemplary active areas of an imaging device provided in the method for performing a cephalometric image according to the first embodiment of the invention.
Figure 3B:
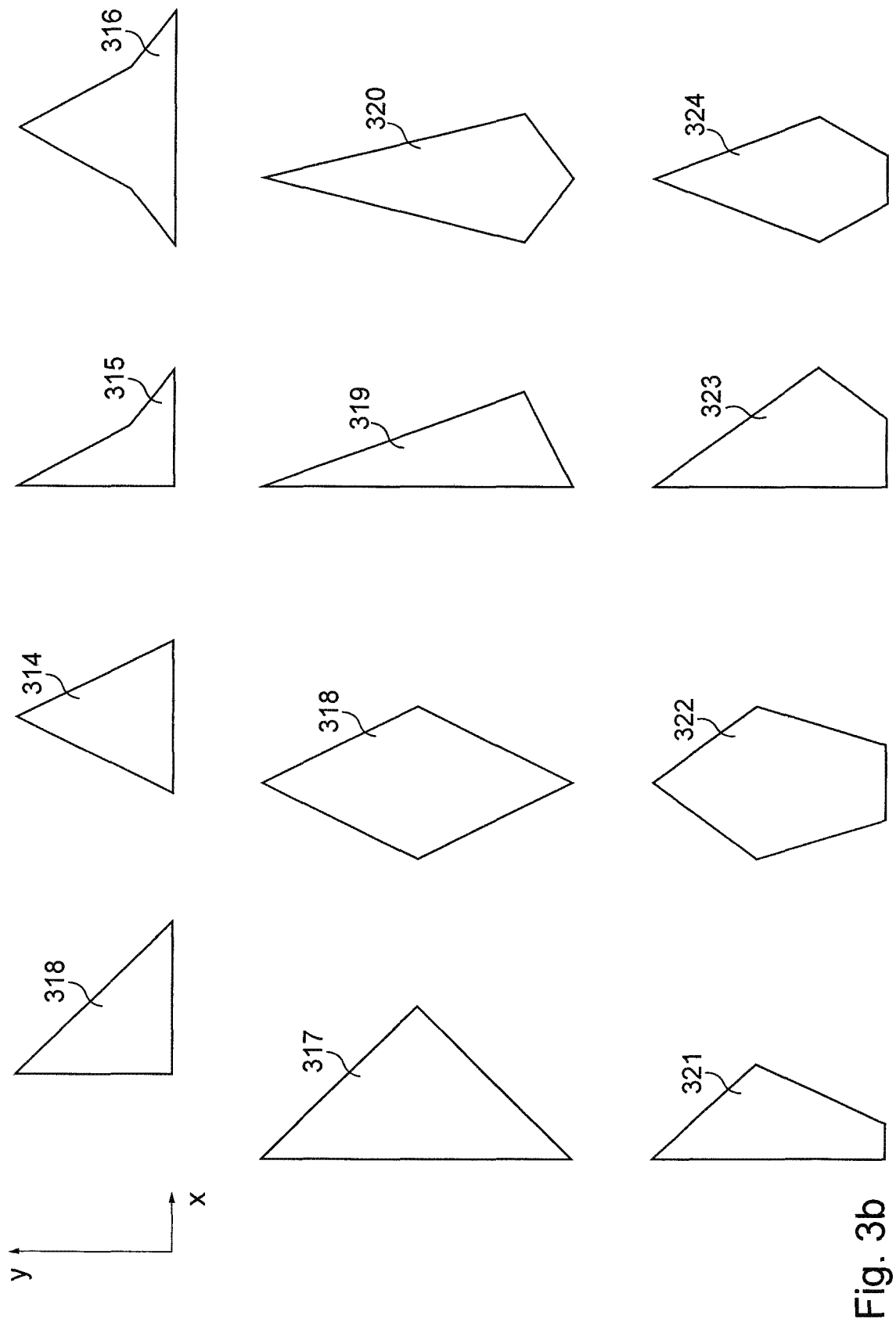

FIGS. 3A and 3B will now be discussed. FIGS. 3A and 3B disclose a number of active surfaces 301 to 324, which represent possible configurations for the active portion of the surface of the sensor of the apparatus, wherein the width of the active area varies along the height of the active area.

The active surfaces 301 to 304 comprise two portions along the Y-direction (i.e. height), each with a different width along the scanning direction X; looking at the surfaces 301 to 312, it is thus apparent that the alignment and relative dimensions of the portions may vary considerably without straying from the scope of the invention.

For instance, in the active surfaces 301 and 302, the height of the two portions is the same, while in the active surfaces 303 and 304 the narrow portion is of a considerably greater height than the wide portion.

Also, in the active surfaces 302 and 304 the surface is configured to be symmetrical in its height dimension, whereas the active surfaces 301 and 303 are asymmetrical.

As an example, the height of the active surfaces 301 to 312 is between 120 mm and 280 mm.

The width of the narrow portion is between 2 mm and 50 mm and the width of the wide portion is between 50 and 140 mm.

The width of the active surface will dictate the depth resolution in a corresponding portion of the image; thus, where the anatomy is scanned with x-rays that are incident on a wide region, that part of the anatomy will be rendered with a high degree of depth resolution, and vice-versa. Thus, in the active surfaces 301-304, the lower portion of the surface where the width is great is positioned to scan the parts of the skull where a greater depth resolution is desired (e.g. the teeth, jaw, and chin area). The rest of the skull is scanned with x-rays incident on the narrower, upper portion of the surface, minimizing the x-ray dosage in areas where a high depth resolution is not necessary (e.g. the cranium).

In this way, the scanning is adapted to give maximum depth resolution in the features of the patient's anatomy where such resolution is necessary for diagnostic et al. purposes by aligning such features with the wide portions of the surface, while minimizing x-ray dosage overall by using a narrow portion of the surface elsewhere.

The active surfaces 305 to 308 demonstrate further possible variations. In each of these active surfaces 305-308, there are three portions: a narrow, upper portion; a wide, central portion; and a narrow, lower portion. This takes the principle of the active surfaces 301-304 one step further.

The upper and lower portions, where the active surfaces 305-308 are narrow, are positioned to image the upper part of the skull and the chin/neck, respectively, while the middle portion is aligned with the patient's jaws and teeth, irradiating them with a high dose but achieving a high depth resolution.

As with the active surfaces 301 and 303, it will be noted that the active surfaces 305 and 307 are asymmetrical in the Y-direction, while the surfaces 306 and 308 are symmetrical. As appropriate, the edges of the portions may be aligned on a common edge, as in e.g. the active surface 311.

It will be noted that in each of the active surfaces 305-308 the upper portion is the same width as the lower portion, and thus realizes the same depth resolution. This need not necessarily be the case, which is illustrated by the active surfaces 309-312. In the active surfaces 309-312, the lower portion is wider than the upper portion, but still narrower than the middle portion. As a result, the portions of the anatomy scanned by the lower portion (e.g. the chin and vertebrae) will have a greater depth resolution than those scanned by the upper portion (e.g. the cranium and the portions of the anatomy scanned by the middle portion (e.g. the teeth) will have a depth resolution greater still. As with the other active surfaces, the active surfaces 309 and 311 are asymmetrical, while the active surfaces 310 and 312 are symmetrical in the Y-direction.

FIG. 3B continues this theme, but rather than the active surfaces 301-312 of FIG. 3A constructed of rectilinear shapes, the active surfaces 313-324 shown in FIG. 3B are formed of triangular or trapezoidal shapes. These triangular or trapezoidal shapes may be defined by their average width, in the same way that the rectilinear portions which form the active surfaces 301-312 are defined by their widths.

In fact, it will be quite apparent to the person of skill in the art that the active surfaces 313-324 correspond to the active surfaces 301-312, respectively, in terms of the positioning of the portions of the active surface and the depth resolution achieved therein. For example, the active surface 322 comprises a narrow upper portion, a wide middle portion, and a lower portion which is narrower than the middle portion but wider than the upper portion, just as does the active surface 310. Symmetry in the Y-direction, or lack thereof, corresponds between the surfaces of FIGS. 3A and 3B.

Thus, by considering the active surface as a plurality of portions, and by adjusting the width of those portions according to the required depth resolution in the corresponding anatomical features to be imaged, the dose of x-rays to the patient is minimized while still maintaining sufficient depth resolution in each part of the image.

Figure 5:
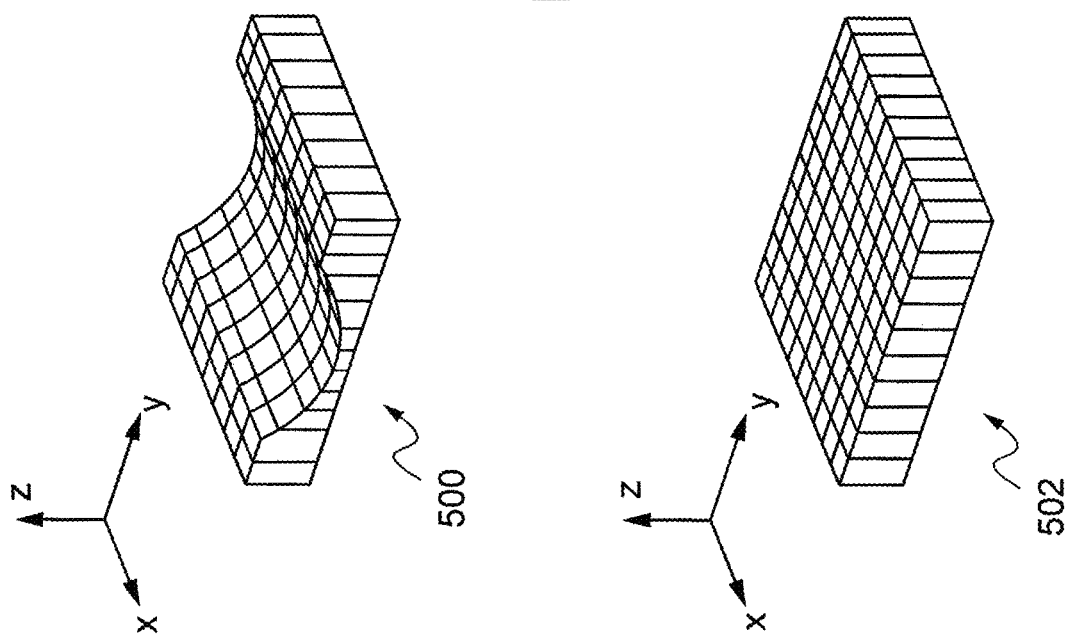
FIG. 5 is an illustration of voxels produced by an imaging device according to a first embodiment of the invention, compared with voxels produced by the same technique with a narrow rectangular sensor.
Figure 4:
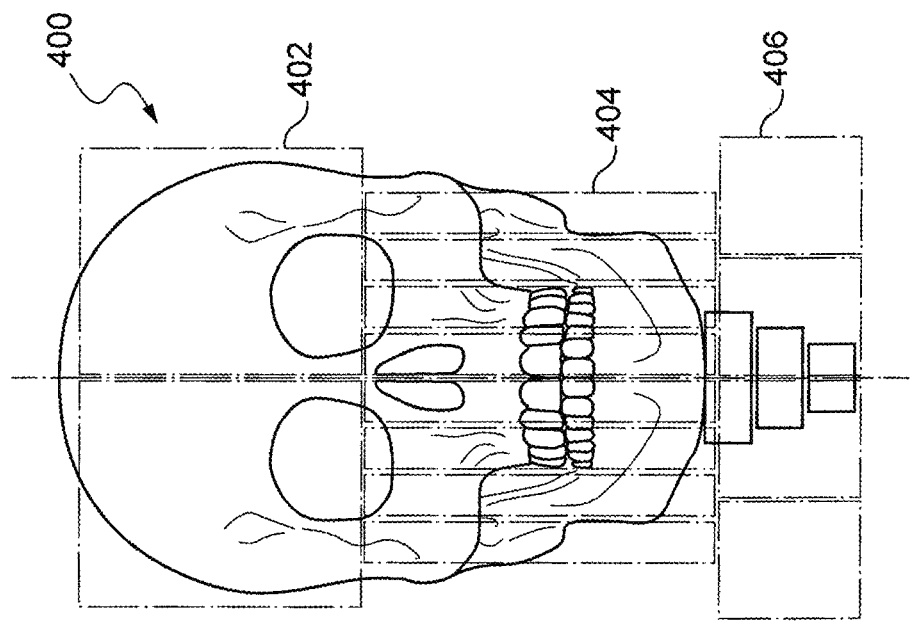
FIG. 4 is an illustration of voxels produced by imaging device according to the first embodiment of the invention, superimposed onto a human skull.

The effect of this is further illustrated in FIGS. 4 and 5. In FIG. 4, there is illustrated a skull 400, superimposed with groups of voxels 402, 404, and 406. The size of the voxels 402, 404, 406 represents the depth resolution realized in that portion of the skull 400: the narrower the voxel in the coronal direction, the wider the corresponding portion of the sensor surface in the scanning direction.

The voxels 402, 404, 406 each correspond to a portion of a sensor surface, such as the active surface 312 illustrated in FIG. 3A. Since the upper portion of the active surface 312 is narrow, the voxel 402, oriented on the cranium, is very large. This reflects the relatively low depth resolution at this part of the patient's anatomy. Conversely, the middle portion of the active surface 312 produces the voxels 404, which are narrow and thus illustrative of the high depth resolution in this part of the skull 400. The lower portion of the active surface 312 produces the voxels 406: since the lower portion has a width between that of the upper and middle portion of the surface 316, the voxels 406 have a width in the coronal direction between those of the voxels 402 and 404.

FIG. 5 further illustrates the difference in depth resolution, with respect to the scan of a CBCT technique as known in the art, as illustrated by voxels 500 and 502.

The voxels 500 are representative of those produced by the imaging techniques of the present invention. The voxel size in the Z-direction illustrates the depth resolution; the larger the voxel is in the Z-direction, the lower the depth resolution.

In the voxels 500, it is quite apparent that the voxel size varies along the Y-axis, in the same way as described with reference to FIG. 4. The concave curve of the voxels corresponds to a sensor surface such as the active surface 306, wherein the upper and lower portions of the active surface 306 have a narrow width and thus a low depth resolution, while the middle portion has a wide width and thus a high depth resolution.

In contrast, the voxels 502 illustrate a uniformly-poor depth resolution when compared to the voxels 500.

Figure 6:
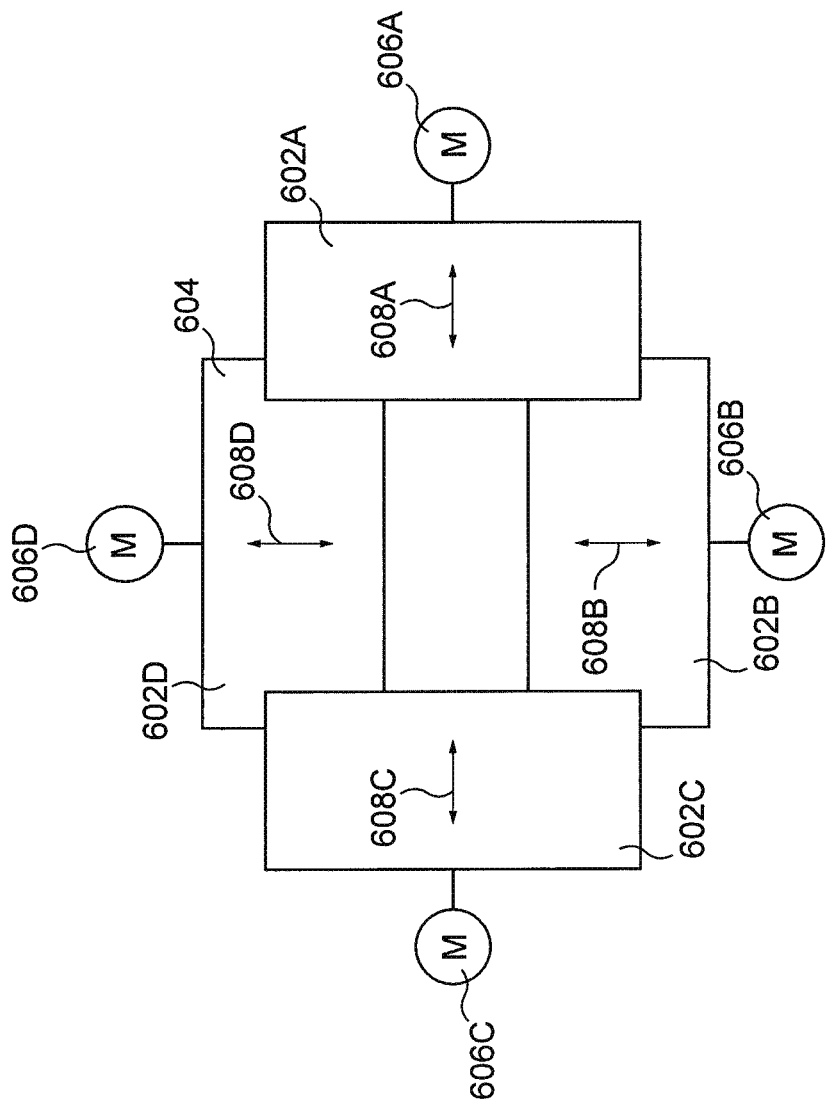
FIG. 6 is an illustration of a collimator for an imaging device according to a first embodiment of the invention.

FIG. 6 illustrates a collimator 600 for a scanning device. The collimator 600 comprises four blades 602A-602D disposed around an orifice 604 through which x-rays are projected at the patient. Each of the blades 602A-602D is mobile by way of a corresponding motor 606A-606D along an axis 608A-608D. In this way, the size and shape of the aperture 604 can be adjusted according to the size and shape of the active surface upon which the x-rays are incident during the scanning process.

In this way, x-ray leakage is minimized, in that one can be assured that little to none of the x-ray energy emitted by the source escapes to the surrounding environment.

The active surfaces (i.e. the irradiated portions of the sensor) 301-312 depicted in FIG. 3A and discussed above can be properly irradiated by disposing two successive collimators in the path of the X-ray beam. In such an embodiment, the aperture of the first (upstream) collimator shapes the beam so that is has a rectangular cross-section.

However, the form of the active surface area that can be realized by a single collimator is limited. More specifically, the collimator can reduce the area of the sensor irradiated by the X-ray beam only so long as the entire active surface is irradiated.

Thus, when the active surface is not a regular quadrilateral (e.g. the active surface area 306 of FIG. 3A), an X-ray beam formed by a single collimator will irradiate the desired active surface 306, but also the portions of the sensor adjoining it, where irradiation is not desired.

The use of a second (downstream) collimator remedies this, in that its blades are positioned to mask portions of the X-ray beam passed by the first collimator corresponding to the non-active portions of the sensor's surface area. In this way, the shape of the X-ray beam is finely controlled so as to irradiate only the active surface area of the sensor, and no more.

Moreover, the second collimator may be configured such that its blades move in a different fashion than the first, offering a greater range of possible beam forms, and thus active surfaces.

Thus, in the example of the active surface 306, four blades of the second (downstream) collimator intercept the "corners" of the rectangular X-ray beam that is passed through the first (upstream) collimator, forming the X-ray beam into the "t" shape of the active surface 306.

The number of collimator blades employed, and the degree to which each of them intercept the X-ray beam, may vary according to the active surface area employed. For instance, an X-ray beam for the active surface 311 can be formed by moving two blades of a second collimator into the X-ray beam: a first one from the top right which impinges the X-ray beam to a relatively large degree, and a second one from the bottom right which intercepts the X-ray beam to a relatively small degree. And for the active surface 301, only a single blade of the second collimator is necessary, intercepting the X-ray beam from the top-right corner.

Variable-blade collimators are thus highly advantageous, in that they can be used to form the X-ray beam according to both the size and the shape of the active surface area employed and by extension, to the patient anatomy to be imaged, in particular the size of the skull which differs greatly between children and adults.

It is also important to note that, while in the collimator 600 the blades 602A-602D move orthogonally to each other, the collimator is not necessarily limited to such motion. Indeed, rotational motion of the blades may be envisioned, for instance where a surface such as one of those depicted in FIG. 3B is used. Moreover, there need not necessarily be four blades; in fact, any number may be used as appropriate to the particular embodiment.

For instance, where the active areas are particularly complex (such as the active surfaces 313-324 depicted in FIG. 3B), it may be preferable to employ a combination of a single collimator downstream of a fixed aperture plate. Because it is fixed, this aperture plate may be configured with a more complex form than might be practical with a mobile-blade collimator. By using such an aperture in conjunction with a collimator as described above, it is possible to form the X-ray beam for more complicated active areas.

Figure 7:
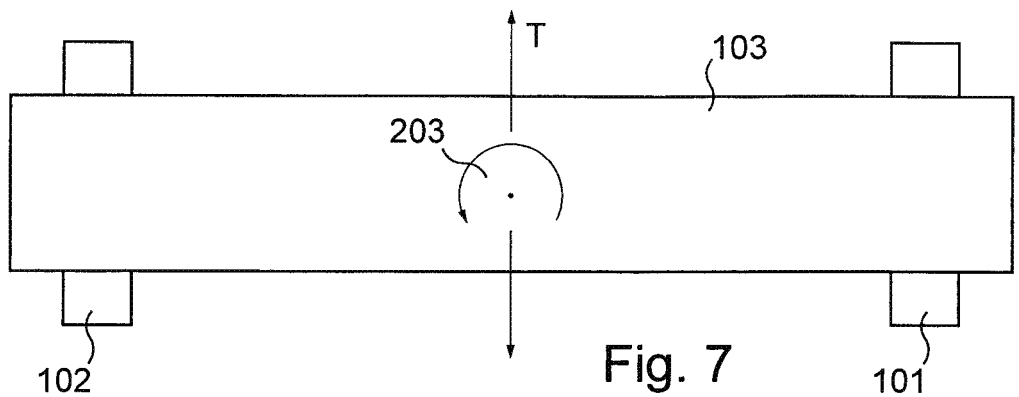
FIG. 7 is an exemplary configuration for a gantry of the imaging system depicted in FIG. 1A.

FIG. 7 illustrates an exemplary configuration for the gantry 103 adapted to displace the X-ray sensor 101 and the X-ray source 102 along the exposure profile previously described.

The gantry 103 is configured to translate laterally along the direction T, as well as to rotate about a central axis of rotation 203. In this embodiment, the gantry 103 is mounted to the horizontal mount 104 through translation and rotation means in order to be able to translate and rotate around the patient 200. For example, in order to perform the exposure profile as depicted in FIG. 2, the gantry 103 comprise a translation mechanism configured to synchronously move the X-ray source 102 and the sensor 101. In one embodiment, the translation mechanism is adapted to translate the gantry 103 with regard to the horizontal mount 104 along the length of the profile exposure.

For example, in order to get a lateral cephalogram, the gantry 103 is translated with the X-ray source 102 and the sensor 101 according to the direction T parallel to the sagittal direction.

This rotation has a range which corresponds to the sweep angle θ as illustrated in FIG. 2.

Moreover, it can be seen in FIG. 2 that the center of rotation 203 of the gantry 103 moves not only in the X-direction (i.e. the sagittal direction), but also moves slightly in the Z-direction (i.e. the coronal direction). This is quite apparent when considering the trajectory of the center of rotation 203, from 203A to 203B, and from 203B to 203C. In any case, the center of rotation 203 of the gantry 103 is positioned above the patient's head and on the same side as the X-ray source 102 (here, on the left side).

To obtain the specific exposure profile, the rotation of the X-ray sensor 101 and the X-ray source 102 and the translation of the gantry 103 are synchronously regulated, for example by controlling means.

The controlling means in an extra-oral dental imaging system, used to control the displacement of the gantry 103 and of the X-ray sensor 101 and the X-ray source 102 are known and will not be described in more details.

In this way, a great deal of control of the incidence of the X-ray beam passing between the X-ray source 102 and the X-ray sensor 101, relative to the patient 200, is achieved. More specifically, the point at which the X-ray beam emitted by the X-ray source 102 is incident upon the patient, as well as the angle of said beam relative to the mid-sagittal plane 206 and/or coronal plane 208 (depicted in FIG. 2) can be readily controlled, as the X-ray beam sweeps through the transverse plane of the patient 200.

Ideally, the sweep angle θ will be between 15° and 30°, as such an angle presents a good balance between patient X-ray dosage and image quality. However, in other applications, such as the imaging of other regions of the body, a different sweep angle θ, either wider or narrower, could equally be envisioned.

The frame rate during the scan is comprised between 15 and 50 frames per second, and most preferably between 15 and 30 frames per second.

High capture frame rates are generally preferable for high depth resolution; however, since the sensor 101 has a large active area and realizes a fine depth resolution, this makes it possible to use a lower frame rate than what might be employed in the art to reduce the amount of raw image data generated, thereby minimizing image-processing computing loads while still maintaining good depth resolution in reconstructed images.

Furthermore, the rotation of the gantry 103 about the axis of rotation 203 permits bilateral imaging without disturbing the position of the patient; the gantry 103 rotates through 180° to reposition the X-ray sensor 101 and the X-ray source 102 to scan the patient 200 from the other side. In addition, the center of rotation 203 of the gantry 103 is displaced in the Z-direction so as to place the center of rotation 203 on the other side of the patient's head 200, and that the patient's head 200 remains in the vicinity of the sensor 101 (see FIG. 2).

This presents a considerable advantage over the cephalographic techniques presently known in the art, in that it produces two separate bilateral images, rather than one single image with superimposed anatomical figures.

Moreover, this is achieved with the same or a small increase in X-ray dosage relative to the cephalographic techniques known in the art, and with a greatly-reduced dosage relative to standard tomographic imaging techniques which irradiate the patient from many different angles, such as Cone Beam Computerized Tomography (CBCT).

By acquiring projections at two opposite angular extremes, separate images for left and right sides of the patient may be obtained: two half cephalometric images, with no superposition, are created with only twice the X-ray's dose of a classic 2D cephalogram.

Figure 8:
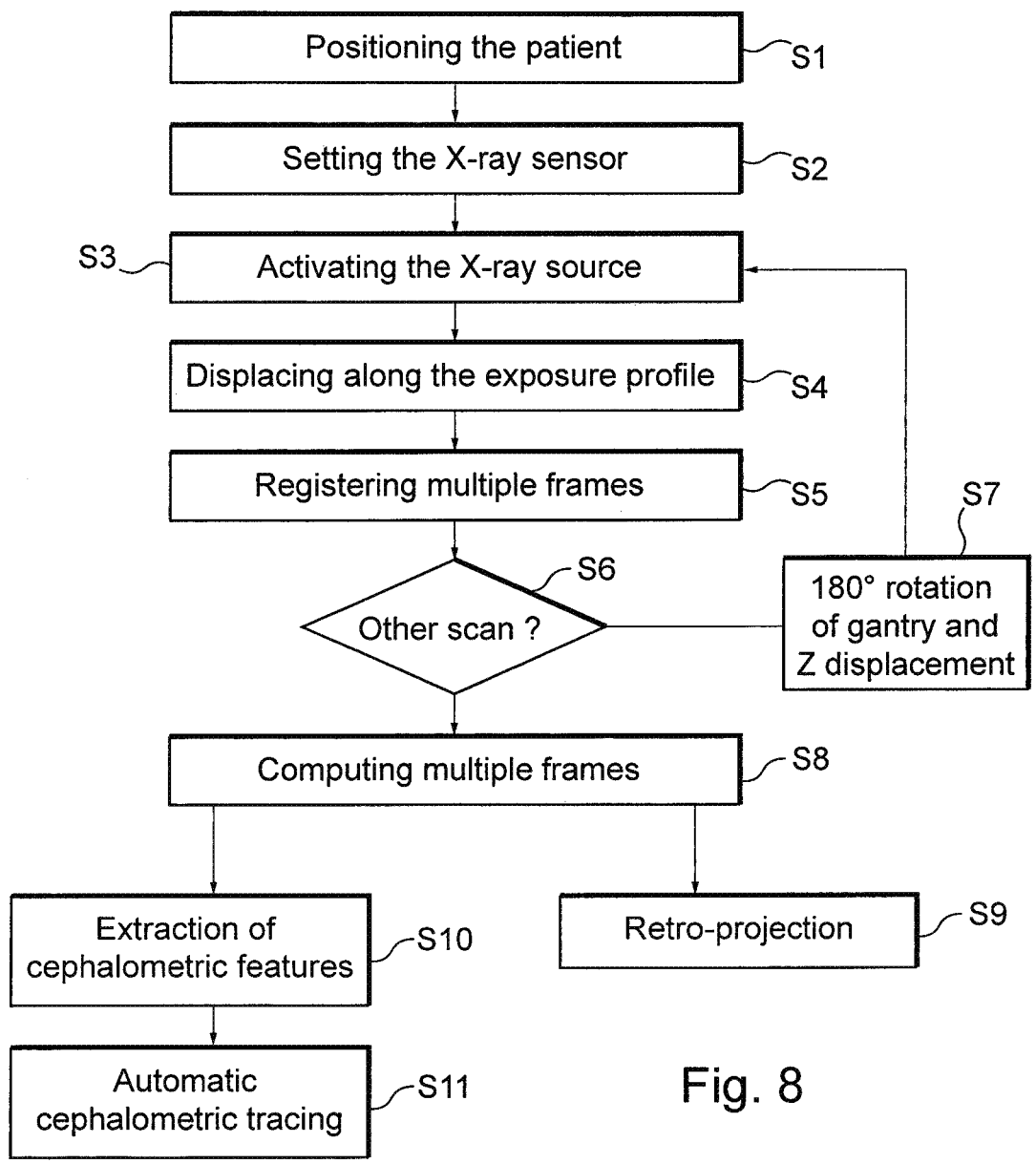
FIG. 8 is a flow chart that shows an exemplary method for performing a cephalometric image according to one embodiment of the invention.

Turning now to FIG. 8, an algorithm which implements the method according to an embodiment of the invention is discussed in further detail.

The method comprises a step for positioning S1 of the patient 200 between the X-ray source 102 and the X-ray sensor 101. This is ideally accomplished by the use of a headrest or brace as the patient holder 106 displayed in FIGS. 1A and 1B, so as to create a proper reference point upon which the data extracted during the scan can be constructed into an image.

A setting step S2 is performed in order to set up the active area 300 of the X-ray sensor 101. As known in prior art, a collimator is used in front of the X-ray source 102 in order to adapt the X-ray beam to the active area 300 of the X-ray sensor 101.

As previously described and depicted in FIGS. 3A and 3B, this active area is determined in order to have a width varying along the height of the active area.

Once the patient is positioned, there is an activating step S3 for activating the X-ray source, followed by a displacing step S4 for sweeping the X-ray beam across the patient. The displacing step S4 involves both synchronously translating and rotating the X-ray source 102 and X-ray sensor 101, thereby sweeping the beam across the patient as depicted in FIG. 2.

The multiple frames produced by the X-ray sensor 101 during the exposure of the skull are registered during a registering step S5.

Optionally, a test S6 is conducted in order to determine if an opposite scan is needed.

In the affirmative, a step S7 for repositioning the X-ray source 102 and X-ray sensor 101 is performed, in which the X-ray source 102 and sensor 101 are rotated through 180° about the patient 200, and the center of rotation 203 displaced in the Z-direction. In this way, the steps of activating S3, displacing S4 and registering S5 for a second scan of the patient 200 are achieved, which are performed in substantially the same way as described above with relation to steps S3 to S5.

Thus, in this embodiment the exposure profile comprises two separate substantially linear sections at two opposite angular extremes about the patient 200.

Once the scan(s) is (are) complete, the method reconstructs the data gathered by the X-ray sensor 101 into a useable image, for reconstructing three-dimensional volumetric data of the patient anatomy.

For this, the method comprises a step S8 of computing the multiple frames produced during at least part of the exposure. This computing step S8 involves applying a shift-and-add processing to reconstruct the image as a series of "slices," each containing a small portion of volumetric data describing the patient's anatomy.

Apart from tomosynthesis, other 3D reconstruction techniques can also be employed. The use of an iterative reconstruction algorithm such as SART (Statistical Algebraic Reconstruction Technique) or SIRT (Statistical Iterative Reconstruction Technique), or a technique like a Filtered Back Projection, to obtain the volumetric data opens up the possibility of obtaining an artifact-free volume with a very low x-ray dose. The Digital Cephalometric Tomosynthesis can be done with a dose between one and two times that of a classic 2D Cephalogram.

Generally, a single plane or the complete volume can be reconstructed using the Shift & Add, Filtered Back Projection, or Iterative techniques.

The Shift & Add algorithm is the fastest method, reconstructing a desired plane or set of planes according to the acquisition trajectory and desired anatomy. The Shift & Add algorithm does require the application of a de-blurring or enhancement filter to the reconstructed image, but is overall economic with computing resources.

The Filtered Back Projection technique is an approach similar to Shift & Add, but with the added possibility of obtaining a complete 3D volume. From this volume views along certain desired planes can then be extracted.

The iterative approaches (e.g. SIRT & SART) use some a priori information about the object, in particular, anatomical a priori information such as selected cranial measurements and/or the limits of the skull in space. The use of a priori information such as these can help compensate for limited angle problems, as well as help reduce the necessary x-ray dosage. However, iterative reconstruction methods are generally slower than other methods.

The reconstructed slices contain in focus imaging data belonging respectively to several depths of the imaged skull.

Figure 9:
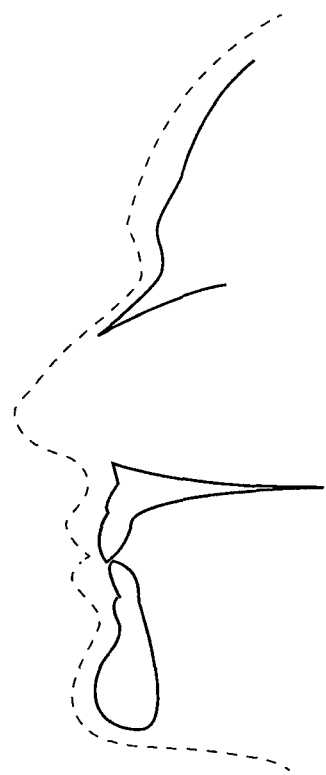
FIG. 9 is an example of the in focus features extracted from a slice on the zero sagittal plane of a human skull.

On the one hand, each slice can be used for the extraction of some cephalometric features. As depicted in FIG. 9, the in focus features extracted from a slice on the mid-sagittal plane of a human skull may be obtained.

Moreover, the extracted features through different depths can be put together to provide a cephalometric image.

Figure 10:
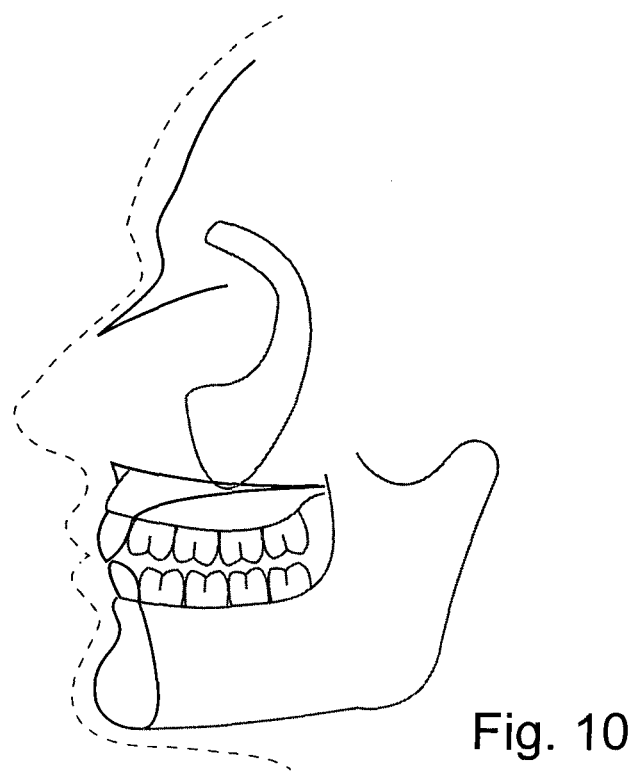
FIG. 10 is an example of the superimposition of the in focus features extracted from all slices belonging to a left part of a human skull.

As shown in FIG. 10, the superimposition of at least some of the in focus features extracted from all slices belonging to a left part of a human skull provides an half cephalometric image for the left side of the patient.

Such a reconstruction is particularly advantageous, in that unlike the methods known in the art, the reconstruction is not limited to a narrow focal trough in which the image is clear and undistorted, but rather each aspect of the patient's anatomy is represented by the slice in which that aspect is displayed with the highest fidelity and resolution. Such a method will ultimately produce an accurate, three-dimensional model of the patient's anatomy while simultaneously minimizing X-ray dosage.

A consequence of this is that a great deal of other, more conventional images can be simulated through simple data processing methods, based on the model produced in the step S8 for reconstructing the 3D volumetric data.

For instance, simulated left and right 2D lateral images, either separate or superimposed, can be constructed by passing the 3D model through a step S9 for retro-projecting, i.e. simulating a standard cephalogram as produced by a "ceph arm"-equipped imaging system through known rendering techniques such as cone beam or parallel geometry projection.

Such a retro-projection might be calibrated to produce a simulated retro-projection distance of between 1.5 m and 4 m, so as to best simulate the images produced by current imaging systems; however it will be understood that other projection distances might also be advantageous in other applications, and that the method of the present invention can easily be so adapted. An infinite projection distance is particularly advantageous, in that it corresponds to a parallel beam projection.

The synthetized 2D cephalogram looks like a standard cephalogram as obtained with a X-ray sensor located on a cephalometric arm of 1.50 m or more related to the position of the X-ray source.

Producing a panoramic image of the mandible and dentition may also be envisioned, performed in a similar way using other, appropriate rendering methods.

These extracted, simulated images can in themselves have important diagnostic and therapeutic uses.

For instance, by extracting the relevant cephalometric features from the 3D model and/or 2D images, and identifying them on said 2D lateral images in an extraction step S10, a cephalometric tracing can be produced at an automatic cephalometric tracing step S11. Such a cephalometric tracing yields valuable diagnostic and therapeutic data, and is much easier and faster to produce than the plaster-molding methods presently employed.

Figure 11:
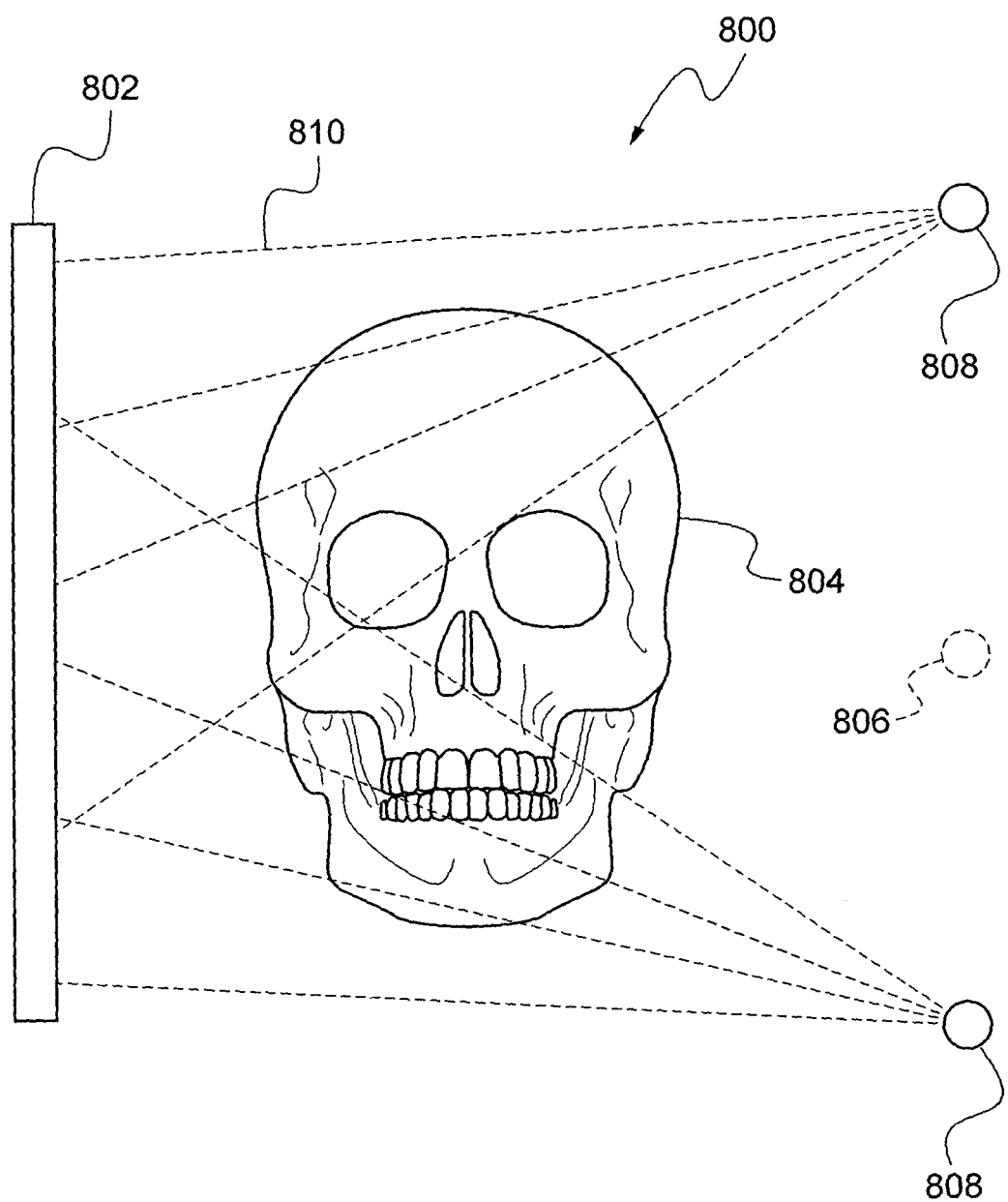
FIG. 11 is an alternative embodiment of an exposure profile performed in a method for creating a cephalometric image.

FIG. 11 illustrates a possible variant of the invention. In FIG. 11, there is provided a scanning apparatus 800 comprising a sensor 802, which is employed for imaging a patient 804.

The sensor 802 is configured according to the above description, in that it has different regions of varying width along its height. For the purposes of illustration, it should be considered that in this embodiment the sensor 802 has an active surface substantially similar in form to the surface 302 of FIG. 3A. However, sensors with active surfaces in other forms may also be envisioned.

With such a sensor it is possible to scan the entirety of the patient's head 804 in one pass, such as by a centrally-located X-ray source 806, as in the other embodiments of the invention discussed above.

In the present embodiment, however, a different approach is employed. Here, an X-ray source 808 is disposed in a first, upper position, from which it irradiates an upper portion of the patient's skull 804 with a beam 810 of X-rays. This beam 810 illuminates only, or at least primarily, the upper portion of the sensor 802, which has a reduced width in the scanning direction as a consequence of the lower degree of depth resolution required to sufficiently image the patient's cranium.

Once this is accomplished, the X-ray source 808 is moved into the lower position, where the scan is repeated. Here, however, the X-ray beam irradiates the lower portion of the skull.

As a result, the X-rays passing through the patient 804 illuminate only, or at least primarily, the lower portion of the sensor 802, which is wider in the scanning direction than the upper portion and thus has a greater depth resolution. In this way, the lower portion of the skull, containing the mandibles, dentition, and other such complex structures, is imaged at high resolution.

The scanning steps may optionally be repeated from the other side of the patient's head 804. There may also be scans performed with the X-ray source 808 disposed in one or more intermediate positions, between the upper and lower positions depicted in FIG. 11, each intermediate position possibly corresponding to a region or regions of the active area of the sensor 802.

Such a method is particularly advantageous in that it allows for a more granular control of the X-ray dose received by the patient 804: in particular, the X-ray beam 810 may be more or less intense, depending on which portion of the patient's anatomy is being scanned and which portion of the active surface of the sensor 802 is being illuminated. In turn, this results in a further refinement of image quality, with an X-ray dosage that, while being slightly greater than other embodiments of the present invention, is nonetheless considerably reduced compared to the techniques known in the art.

In any case, the resulting images are combined, such as by stitching or other such image processing techniques, so as to create a finished three-dimensional scan of the patient 804.

The invention claimed is:

1. A method for creating a cephalometric image of at least part of a human skull using an extra-oral dental imaging system having a conical shape x-ray beam and no cephalometric arm, said system comprising:
an X-ray source for producing a conical shape x-ray beam used to irradiate an object to be imaged;
an imaging device suitable for producing multiple frames during at least part of an exposure of said object;
a manipulator for displacing the imaging device along an exposure profile between multiple frames during said at least part of the exposure of said object, the manipulator permitting the movement of the imaging device along a scanning direction (X),
wherein the method comprises the steps of:
setting said imaging device with an active area having in an imaging plane a width extending along said scanning direction (X), said width varying along a height direction (Y) perpendicular to said scanning direction (X);
synchronously displacing the X-ray source and the imaging device along said exposure profile;
modifying the conical shape of said conical shape x-ray beam during displacement of the X-ray source and the imaging device to vary along a height direction (Y) perpendicular to said scanning direction (X); and registering said multiple frames produced by the imaging device during the exposure of said object to be imaged.

2. A method according to claim 1, wherein said active area is symmetric in said imaging plane, with a central axis extending along said height direction (Y) of said active area.

3. A method according to claim 1, wherein said active area has at least two portions having widths different from each other, said two portions being superposed in said imaging plane along said height direction (Y).

4. A method according to claim 3, wherein the height of said active area is between 120 mm and 280 mm, the width of a first portion is between 2 mm and 50 mm, and the width of a second portion is between 50 and 140 mm.

5. A method according to claim 1, wherein said active area has at least three portions with respectively three different widths.

6. A method according to claim 1, wherein said active area has a central portion, a lower portion, and an upper portion each extending along said height direction (Y) in said imaging plane, the width of the central portion is larger than the width of the lower portion and the width of the lower portion is larger than the width of the upper portion.

7. A method according to claim 1, further comprising a step of computing said multiple frames produced during at least one part of the exposure:
by a shift-and-add processing, thereby reconstructing at least one slice; or
by a volumetric approach, thereby reconstructing a three-dimensional volume and subsequently extracting at least one slice from this volume;
wherein said at least one slice includes in-focus imaging data belonging respectively to at least one depth of said object to be imaged.

8. A method according to claim 7, wherein the volumetric approach is selected from a Statistical Algebraic Reconstruction Technique (SART), a Statistical Iterative Reconstruction Technique (SIRT), or a Filtered Back Projection technique.

9. A method according to claim 7, further comprising a step of using each reconstructed slice for the extraction of cephalometric features.

10. A method according to claim 9, further comprising a step of automatic cephalometric tracing, wherein said extracted cephalometric features of each slice are put together.

11. A method according to claim 9, wherein several slices are reconstructed and combined to give a separate linear projection for the left and right sides of said object to be imaged.

12. A method according to claim 7, wherein several slices are reconstructed and retro projected to a distance superior to 1.50 meters, and preferably superior to 4 meters, on a cone beam or parallel geometry so as to create a synthesized 2D cephalogram of the skull.

13. A method according to claim 1, comprising the following steps:
synchronously displacing the X-ray source and the imaging device along a first part of said exposure profile, said X-ray source being in an upper position along said height direction (Y);
registering said multiple frames produced by the imaging device during said first part of the exposure profile;
synchronously displacing the X-ray source and the imaging device along a second part of said exposure profile, said X-ray source being in a lower position along said height direction (Y);
registering said multiple frames produced by the imaging device during said second part of the exposure profile; and
combining said multiple frames registered during said first and second parts of the exposure profile.

14. The method according to claim 1, wherein the step of modifying the conical shape of said conical shape x-ray beam includes modifying the conical shape of said conical shape x-ray beam to conform to the shape of the active area of said imaging device.

15. The method according to claim 1, wherein the step of synchronously displacing said X-ray source and said imaging device along said exposure profile includes a step of synchronously rotating said X-ray source and said imaging device through an angle while translating said X-ray source and said imaging device.

16. The method according to claim 15, wherein the angle has an angular measure between zero degrees and thirty degrees.

17. An extra-oral dental imaging system having a conical shape x-ray beam for creating a cephalometric image of at least part of a human skull without using a cephalometric arm, said system comprising:
an X-ray source for producing said conical shape x-ray beam for irradiating an object to be imaged;
an imaging device suitable for producing multiple frames during at least part of an exposure of said object;
a manipulator for displacing the imaging device along an exposure profile between multiple frames during said at least part of the exposure of said object, the manipulator permitting the movement of the imaging device along a scanning direction (X); and
a collimator;
wherein said imaging device has an active area having in an imaging plane a width extending along said scanning direction (X), said width varying along a height direction (Y) perpendicular to said scanning direction (X);
wherein in that said manipulator is configured to synchronously displace the X-ray source and the imaging device along said exposure profile using translation and rotation of the X-ray source and the imaging device; and
wherein said collimator is configured to modify the shape of said conical shape x-ray beam to vary in unison with varying of said width of said imaging plane along the height direction (Y) perpendicular to said scanning direction (X).

18. The system according to claim 17, wherein said manipulator is configured to rotate the X-ray source and the imaging device in unison through an angle having an angular measure between zero and thirty degrees during displacement of the X-ray source and the imaging device along the exposure profile.

19. A method for creating a cephalometric image of at least part of a human skull using a cone beam computed tomography (CBCT) extraoral imaging system without a cephalometric arm, the method comprising the steps of:
generating, via an X-ray source, an x-ray beam having a conical shape to irradiate an object to be imaged;
producing, via an imaging device, multiple image frames during at least part of an exposure of said object to the x-ray beam, wherein the imaging device has an active area;
moving the X-ray source and the imaging device in unison along an exposure profile in a scanning direction (X) between multiple image frames during said at least part of the exposure of said object, wherein the active area of the imaging device has a width extending along the scanning direction (X) and varying along a height direction (Y) perpendicular to the scanning direction (X);

rotating the X-ray source and the imaging device in unison through a limited angle while moving along the exposure profile; and registering the multiple frames produced by the imaging device during the exposure of said object to be imaged.

20. The method of claim 19, wherein the limited angle has an angular measure between zero and thirty degrees.

21. The method of claim 19, wherein the method further comprises a step of modifying the conical shape of the produced x-ray beam during movement of the X-ray source and the imaging device to produce an x-ray beam having a shape varying in conformity with the variation of the width of the active area of the imaging device.

* * * * *